United States Patent
Ohuchida et al.

(10) Patent No.: US 6,235,780 B1
(45) Date of Patent: May 22, 2001

(54) ω-CYCLOALKYL-PROSTAGLANDIN $E_1$ DERIVATIVES

(75) Inventors: Shuichi Ohuchida; Kousuke Tani, both of Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/356,674

(22) Filed: Jul. 19, 1999

(30) Foreign Application Priority Data

Jul. 21, 1998 (JP) .................................. 10-221054

(51) Int. Cl.[7] ..................... A61K 31/215; C07C 69/74; C07C 405/00
(52) U.S. Cl. ..................... 514/530; 514/573; 514/623; 560/121; 562/503; 564/189
(58) Field of Search ..................... 514/530, 573, 514/623; 560/121; 562/503; 564/189

(56) References Cited

U.S. PATENT DOCUMENTS

| | | | |
|---|---|---|---|
| 4,132,738 | 1/1979 | Kluender et al. | 260/586 |
| 4,444,788 | 4/1984 | Skuballa et al. | 424/305 |
| 4,454,339 | 6/1984 | Skuballa et al. | 560/55 |
| 4,789,685 | 12/1988 | Skuballa et al. | 560/121 |
| 5,079,259 | 1/1992 | Skuballa et al. | 514/530 |
| 5,204,371 | 4/1993 | Skuballa et al. | 514/530 |
| 5,756,818 | * 5/1998 | Buchmann et al. | |

* cited by examiner

Primary Examiner—Howard C. Lee
Assistant Examiner—Leigh C. Maier
(74) Attorney, Agent, or Firm—Stevens, Davis, Miller & Mosher, L.L.P.

(57) ABSTRACT

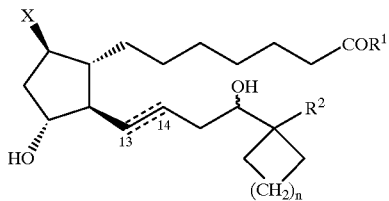

(I)

(wherein $R^1$ is OH etc.; X is Cl, F; $R^2$ is H, C1–8 alkyl, C2–8 alkenyl, C2–8 alkynyl which may be substituted; n is 0–4.), non-toxic salts thereof or cyclodextrin clathrates thereof can strongly bind on $EP_2$ subtype receptor. Therefore, they are useful for the prevention and/or treatment of immunological diseases (autoimmune diseases, post-transplantation graft rejection etc.), asthma, abnormal bone formation, neuronal cell death, hepatopathy, abortion, premature birth or retina neuropathy (e.g. glaucoma) etc.

19 Claims, No Drawings

ω-CYCLOALKYL-PROSTAGLANDIN E₁ DERIVATIVES

FIELD OF INVENTION

This invention relates to ω-cycloalkyl-prostaglandin $E_1$ derivatives.

BACKGROUND

Prostaglandin $E_2$ (abbreviated as $PGE_2$ hereafter.) has been known as a metabolite in the arachidonic acid cascade. It has been known that $PGE_2$ has cyto-protective activity, uterine contractile activity, a pain-inducing effect, a promoting effect of digestive peristalsis, an awaking effect, a suppressive effect of gastric acid secretion, hypotensive activity and diuretic activity etc.

In the recent studies, it was found that $PGE_2$ receptor was divided into some subtypes which possess different physiological roles from each other. At present, four main receptor subtypes are known and they are called $EP_1$, $EP_2$, $EP_3$ and $EP_4$ (Negishi M. et al., J. Lipid Mediators Cell Signaling, 12, 379–391 (1995)).

The present inventors investigated to find new compounds which bind on each receptor specifically, so that we found that the compounds of the present invention could bind strongly on $EP_2$ subtype receptor and achieved the present invention.

The compounds of the present invention of formula (I) possess a strong binding activity for $EP_2$ subtype receptor. Therefore, they are useful for the prevention and/or treatment of immunological diseases (autoimmune diseases, post-transplantation graft rejection etc.), asthma, abnormal bone formation, neuronal cell death, hepatopathy, abortion, premature birth or retina neuropathy (e.g. glaucoma) etc.

Among the compounds of the present invention of formula (I), compounds which bind weakly on other receptor subtypes than $EP_2$ and other receptors of arachidonic acid metabolites (thromboxane receptor, $PGI_2$ receptor etc.) do not express other effects and therefore, it is probable that those compounds will be medical agents which have less side-effects.

On the other hand, many patent applications of PG derivatives are known. The following applications are mentioned for example.

(1) In the specification of JP54-115351 (i.e. U.S. Pat. No. 4,132,738), a compound of formula (A)

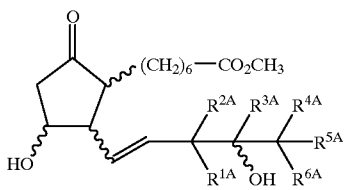

(A)

(wherein $R^{1A}$ and $R^{2A}$ are hydrogen; $R^{3A}$ is hydrogen or is taken together with $R^{4A}$ to form a methylene chain of 4 carbon atoms wherein a cycloalkyl of 6 carbon atoms inclusive is formed, or is taken together with $R^{4A}$ to form a bicycloalkenyl or bicycloalkyl moiety having the formula

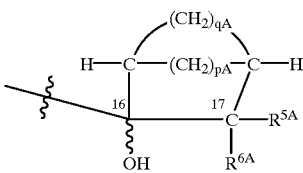

(wherein pA is an integer having a value of from 0 to 1 and qA is an integer having a value of from 2 to 3 and wherein the double-bond of such bicycloalkenyl is in the qA bridge.); $R^{4A}$ is taken together with $R^{3A}$ to form a cycloalkyl, bicycloalkyl or bicycloalkenyl as defined above, or is taken together with $R^{5A}$ to form a methylene chain of 3 carbon atoms wherein a cycloalkyl of 4 carbon atoms inclusive is formed; $R^{5A}$ is hydrogen, or is taken together with $R^{4A}$ to form a cycloalkyl as defined above; and $R^{6A}$ is hydrogen or straight-chain alkyl having 8 carbon atoms.) are disclosed as having prostaglandin like activity.

(2) In the specification of JP56-92860, a compound of formula (B)

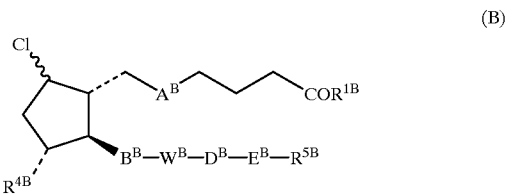

(B)

(wherein chlorine atom at 9-position may be attached to α- or β-position; $R^{1B}$ is $OR^{2B}$ ($R^{2B}$ is hydrogen atom, alkyl, cycloalkyl, aryl or heterocyclic group) or $NHR^{3B}$ ($R^{3B}$ is acidic residue or hydrogen); $A^B$ is —$CH_2$—$CH_2$— or cis-CH=CH—; $B^B$ is —$CH_2$—$CH_2$—, trans-CH=CH— or —C≡C—; $W^B$ is free or functionalized form of hydroxymethylene or free or functionalized form of —C(OH)($CH_3$)— (OH may be attached to α- or β-position); $D^B$ and $E^B$ are taken together to represent bond or $D^B$ is C1–10 straight-chain or branched-chain alkylene; $E^B$ is oxygen, sulfur atom or bond; $R^{4B}$ is free or functionalized form of hydroxy; $R^{5B}$ is alkyl, alkyl substituted by halogen, cycloalkyl, substituted or unsubstituted aryl or heterocyclic group.) is described.

(3) In the specification of JP58-8059, a compound of formula (C)

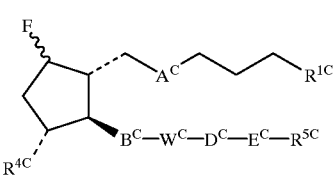

(C)

(wherein $R^{1C}$ is —$CH_2OH$, —$COOR^{2C}$ ($R^{2C}$ is hydrogen atom, alkyl which may be substituted, cycloalkyl, aryl or heterocyclic group which may be substituted by alkyl), —$CONHR^{3C}$ ($R^{3C}$ is acidic residue or $R^{2C}$); $A^C$ is —$CH_2$—$CH_2$— or cis-CH=CH—; $B^C$ is —$CH_2$—$CH_2$—, trans-CH=CH— or —C≡C—; $W^C$ is free or functionalized form of hydroxymethylene; $D^C$ and $E^C$ are taken together to form bond, or $D^C$ is C1~10 straight-chain or branched-chain alkylene which may be substituted by fluorine atom, $E^C$ is oxygen atom, sulfur atom, bond, —C≡C—, —CR$^{6C}$=CR$^{7C}$—(R$^{6C}$ and R$^{7C}$ are different to represent hydrogen atom, chlorine atom or alkyl), R$^{4C}$ is free or functionalized form of hydroxy, R$^{5C}$ is hydrogen atom, halogen or alkyl which may be substituted by aryl which may be substituted, cycloalkyl, aryl or heterocyclic group which may be substituted by alkyl.) is described.

DISCLOSURE OF THE INVENTION

The present invention provides an ω-cycloalkyl-prostaglandin E$_1$ derivative of formula (I)

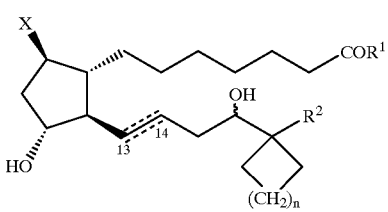

(I)

wherein R$^1$ is hydroxy, C1–6 alkoxy or NR$^{11}$R$^{12}$ wherein R$^{11}$ and R$^{12}$ are independently hydrogen atom or C1–6 alkyl;
X is chlorine atom or fluorine atom;
R$^2$ is hydrogen atom, C1–8 alkyl, C2–8 alkenyl or C2–8 alkynyl, or C1–8 alkyl, C2–8 alkenyl or C2–8 alkynyl substituted by 1–3 of the following groups (1)–(5);
(1) halogen atom,
(2) C1–4 alkoxy,
(3) C3–7 cycloalkyl,
(4) phenyl or
(5) phenyl substituted by 1–3 substituents selected from halogen atom, C1–4 alkyl, C1–4 alkoxy, nitro and trifluoromethyl;
n is 0–4; and

is single-bond, double-bond or triple-bond; or a non-toxic salt thereof or cyclodextrin clathrate thereof.

In formula (I), C1–4 alkyl represented by the substituents in R$^2$ means methyl, ethyl, propyl, butyl and isomers thereof.

In formula (I), C1–6 alkyl represented by R$^{11}$ and R$^{12}$ means methyl, ethyl, propyl, butyl, pentyl, hexyl and isomers thereof.

In formula (I), C1–8 alkyl represented by R$^2$ means methyl, ethyl, propyl, butyl, pentyl, hexyl, heptyl, octyl and isomers thereof.

In formula (I), C2–8 alkenyl represented by R$^2$ means vinyl, propenyl, butenyl, pentenyl, hexenyl, heptenyl, octenyl and isomers thereof.

In formula (I), C2–8 alkynyl represented by R$^2$ means ethynyl, propynyl, butynyl, pentynyl, hexynyl, heptynyl, octynyl and isomers thereof.

In formula (I), C1–4 alkoxy represented by the substituents in R$^2$ means methoxy, ethoxy, propoxy, butoxy and isomers thereof.

In formula (I), C1–6 alkoxy represented by R$^1$ means methoxy, ethoxy, propoxy, butoxy, pentyloxy, hexyloxy and isomers thereof.

In formula (I), C3–7 cycloalkyl represented by the substituents in R$^2$ means cyclopropyl, cyclobutyl, cyclopentyl, cyclohexyl and cycloheptyl.

In formula (I), halogen atom represented by the substituents in R$^2$ means fluorine, chlorine, bromine and iodine.

In the present invention, R1 is preferably hydroxy or methoxy.

R2 is preferably C1–4 alkyl, C2–4 alkenyl or C2–4 alkynyl, or C1–4 alkyl, C2–4 alkenyl or C2–4 alkynyl substituted by 1–3 of the groups (1)–(5).

The halogen atom substituent in the definition of R2 is preferably chlorine or fluorine.

The C1–4 alkoxy substituent in the definition of R2 is preferably methoxy.

The C3–7 cycloalkyl substituent in the definition of R2 is preferably cyclopropyl or cyclohexyl.

R2 is most preferably ethyl.

n is preferably 0 or 1, more preferably 1.

In the present invention, as may be easily understood by those skilled in the arts, unless otherwise specified, the symbol:

indicates that the substituent attached thereto is in front of the sheet, unless otherwise specified, the symbol:

indicates that the substituent attached thereto is behind the sheet, unless otherwise specified, the symbol:

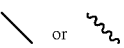

indicates that the substituent attached thereto is in front of or behind the sheet or is a mixture thereof.

Unless otherwise specified, all isomers are included in the present invention. For example, the alkyl, alkenyl and alkynyl groups include straight-chain and branched-chain ones. The double-bond in alkenyl group include E, Z and EZ mixture ones. Isomers generated by the existence of asymmetric carbon atom(s) (e.g. when branched chain alkyl exists) are included in the present invention.

Preferred compounds of the present invention of formula (I) include the compounds listed in the Examples and in Tables 1–6, and non-toxic salts thereof.

TABLE 1
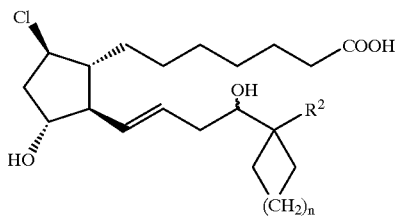
(I-1)
| No. | n | —R₂ | No. | n | —R₂ |
|---|---|---|---|---|---|
| 1 | 0 | ethyl | 17 | 1 | ethyl |
| 2 | 0 | n-propyl | 18 | 1 | n-propyl |
| 3 | 0 | n-butyl | 19 | 1 | n-butyl |
| 4 | 0 | isopropyl | 20 | 1 | isopropyl |
| 5 | 0 | vinyl | 21 | 1 | vinyl |
| 6 | 0 | allyl | 22 | 1 | allyl |
| 7 | 0 | but-3-enyl | 23 | 1 | but-3-enyl |
| 8 | 0 | but-2-ynyl | 24 | 1 | but-2-ynyl |
| 9 | 0 | 3-chloropropyl | 25 | 1 | 3-chloropropyl |
| 10 | 0 | 4-chlorobutyl | 26 | 1 | 4-chlorobutyl |
| 11 | 0 | 4-fluorobutyl | 27 | 1 | 4-fluorobutyl |
| 12 | 0 | 3-methoxypropyl | 28 | 1 | 3-methoxypropyl |
| 13 | 0 | cyclopropylmethyl | 29 | 1 | cyclopropylmethyl |
| 14 | 0 | cyclohexylmethyl | 30 | 1 | cyclohexylmethyl |
| 15 | 0 | benzyl | 31 | 1 | benzyl |

TABLE 1-continued
(I-1)
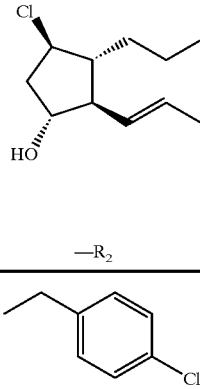
| No. | n | —R₂ | No. | n | —R₂ |
|---|---|---|---|---|---|
| 16 | 0 | 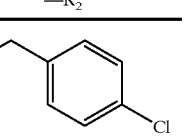 | 32 | 1 | 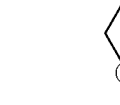 |
TABLE 2
(I-2)
| No. | n | —R₂ | No. | n | —R₂ |
|---|---|---|---|---|---|
| 1 | 0 | 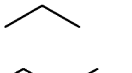 | 17 | 1 | 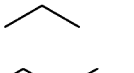 |
| 2 | 0 | 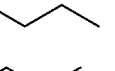 | 18 | 1 | 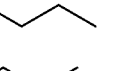 |
| 3 | 0 | 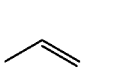 | 19 | 1 | 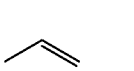 |
| 4 | 0 | 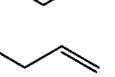 | 20 | 1 | 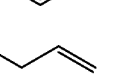 |
| 5 | 0 | 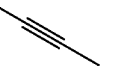 | 21 | 1 | 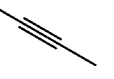 |
| 6 | 0 | 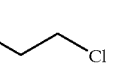 | 22 | 1 | 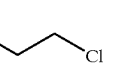 |
| 7 | 0 |  | 23 | 1 |  |
| 8 | 0 |  | 24 | 1 |  |
| 9 | 0 | ⌒⌒⌒Cl | 25 | 1 | ⌒⌒⌒Cl |
| 10 | 0 | ⌒⌒⌒⌒Cl | 26 | 1 | ⌒⌒⌒⌒Cl |
| 11 | 0 | ⌒⌒⌒⌒F | 27 | 1 | ⌒⌒⌒⌒F |

TABLE 2-continued (I-2)

| No. | n | —R$_2$ | No. | n | —R$_2$ |
|---|---|---|---|---|---|
| 12 | 0 | propyl-O-methyl | 28 | 1 | propyl-O-methyl |
| 13 | 0 | ethyl-cyclopropyl | 29 | 1 | ethyl-cyclopropyl |
| 14 | 0 | ethyl-cyclohexyl | 30 | 1 | ethyl-cyclohexyl |
| 15 | 0 | ethyl-phenyl | 31 | 1 | ethyl-phenyl |
| 16 | 0 | ethyl-(4-chlorophenyl) | 32 | 1 | ethyl-(4-chlorophenyl) |

TABLE 3

(I-3)

| No. | n | —R$_2$ | No. | n | —R$_2$ |
|---|---|---|---|---|---|
| 1 | 0 | propyl | 17 | 1 | propyl |
| 2 | 0 | butyl | 18 | 1 | butyl |
| 3 | 0 | pentyl | 19 | 1 | pentyl |
| 4 | 0 | isobutyl | 20 | 1 | isobutyl |

TABLE 3-continued
(I-3)
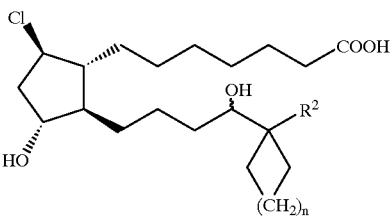
| No. | n | —R₂ | No. | n | —R₂ |
|---|---|---|---|---|---|
| 5 | 0 |  | 21 | 1 |  |
| 6 | 0 |  | 22 | 1 |  |
| 7 | 0 |  | 23 | 1 |  |
| 8 | 0 |  | 24 | 1 |  |
| 9 | 0 |  | 25 | 1 |  |
| 10 | 0 |  | 26 | 1 |  |
| 11 | 0 |  | 27 | 1 |  |
| 12 | 0 |  | 28 | 1 |  |
| 13 | 0 |  | 29 | 1 |  |
| 14 | 0 |  | 30 | 1 |  |
| 15 | 0 |  | 31 | 1 |  |
| 16 | 0 |  | 32 | 1 |  |

TABLE 4
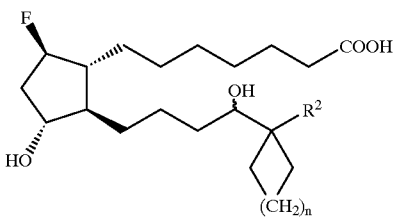
(I-4)
| No. | n | —R₂ | No. | n | —R₂ |
|---|---|---|---|---|---|
| 1 | 0 | ethyl | 17 | 1 | ethyl |
| 2 | 0 | propyl | 18 | 1 | propyl |
| 3 | 0 | butyl | 19 | 1 | butyl |
| 4 | 0 | isopropyl | 20 | 1 | isopropyl |
| 5 | 0 | vinyl | 21 | 1 | vinyl |
| 6 | 0 | allyl | 22 | 1 | allyl |
| 7 | 0 | but-3-enyl | 23 | 1 | but-3-enyl |
| 8 | 0 | but-2-ynyl | 24 | 1 | but-2-ynyl |
| 9 | 0 | —CH₂CH₂CH₂Cl | 25 | 1 | —CH₂CH₂CH₂Cl |
| 10 | 0 | —CH₂CH₂CH₂CH₂Cl | 26 | 1 | —CH₂CH₂CH₂CH₂Cl |
| 11 | 0 | —CH₂CH₂CH₂CH₂F | 27 | 1 | —CH₂CH₂CH₂CH₂F |
| 12 | 0 | —CH₂CH₂CH₂OCH₃ | 28 | 1 | —CH₂CH₂CH₂OCH₃ |
| 13 | 0 | —CH₂-cyclopropyl | 29 | 1 | —CH₂-cyclopropyl |
| 14 | 0 | —CH₂-cyclohexyl | 30 | 1 | —CH₂-cyclohexyl |
| 15 | 0 | —CH₂-phenyl | 31 | 1 | —CH₂-phenyl |

TABLE 4-continued
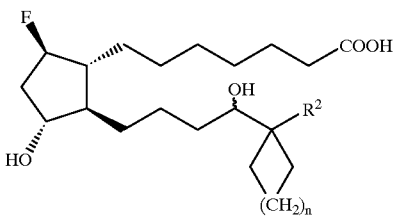
(I-4)
| No. | n | —R₂ | No. | n | —R₂ |
|---|---|---|---|---|---|
| 16 | 0 | 4-Cl-phenylethyl | 32 | 1 | 4-Cl-phenylethyl |
TABLE 5
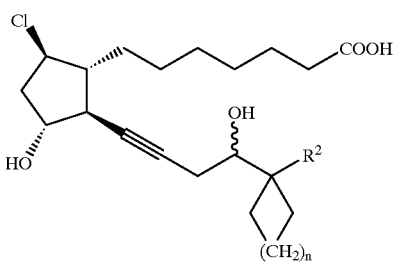
(I-5)
| No. | n | —R₂ | No. | n | —R₂ |
|---|---|---|---|---|---|
| 1 | 0 | ethyl | 17 | 1 | ethyl |
| 2 | 0 | propyl | 18 | 1 | propyl |
| 3 | 0 | butyl | 19 | 1 | butyl |
| 4 | 0 | isopropyl | 20 | 1 | isopropyl |
| 5 | 0 | vinyl | 21 | 1 | vinyl |
| 6 | 0 | allyl | 22 | 1 | allyl |
| 7 | 0 | 3-butenyl | 23 | 1 | 3-butenyl |
| 8 | 0 | 2-butynyl | 24 | 1 | 2-butynyl |
| 9 | 0 | 3-chloropropyl | 25 | 1 | 3-chloropropyl |
| 10 | 0 | 4-chlorobutyl | 26 | 1 | 4-chlorobutyl |

TABLE 5-continued
(I-5)
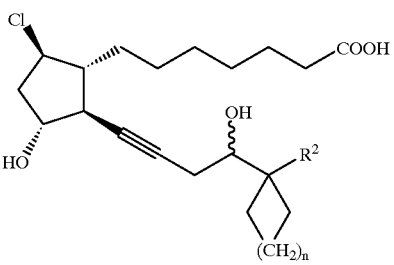
| No. | n | —R₂ | No. | n | —R₂ |
|---|---|---|---|---|---|
| 11 | 0 | 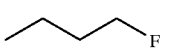 | 27 | 1 | 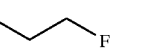 |
| 12 | 0 | 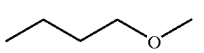 | 28 | 1 | 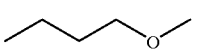 |
| 13 | 0 |  | 29 | 1 |  |
| 14 | 0 | 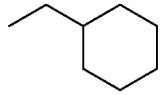 | 30 | 1 | 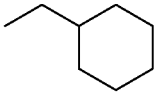 |
| 15 | 0 | 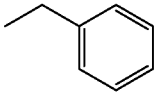 | 31 | 1 | 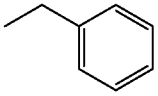 |
| 16 | 0 | 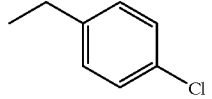 | 32 | 1 | 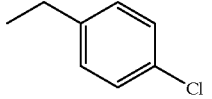 |
TABLE 6
(I-6)
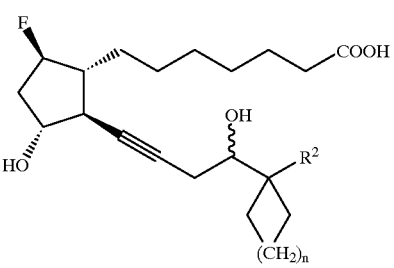
| No. | n | —R₂ | No. | n | —R₂ |
|---|---|---|---|---|---|
| 1 | 0 |  | 17 | 1 |  |
| 2 | 0 | 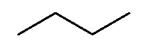 | 18 | 1 | 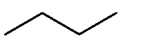 |
| 3 | 0 | 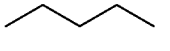 | 19 | 1 | 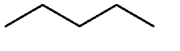 |

TABLE 6-continued (I-6)

| No. | n | —R₂ | No. | n | —R₂ |
|---|---|---|---|---|---|
| 4 | 0 | isobutyl | 20 | 1 | isobutyl |
| 5 | 0 | allyl | 21 | 1 | allyl |
| 6 | 0 | but-3-enyl | 22 | 1 | but-3-enyl |
| 7 | 0 | pent-4-enyl | 23 | 1 | pent-4-enyl |
| 8 | 0 | pent-3-ynyl | 24 | 1 | pent-3-ynyl |
| 9 | 0 | 3-chloropropyl | 25 | 1 | 3-chloropropyl |
| 10 | 0 | 4-chlorobutyl | 26 | 1 | 4-chlorobutyl |
| 11 | 0 | 4-fluorobutyl | 27 | 1 | 4-fluorobutyl |
| 12 | 0 | 4-methoxybutyl | 28 | 1 | 4-methoxybutyl |
| 13 | 0 | cyclopropylmethyl | 29 | 1 | cyclopropylmethyl |
| 14 | 0 | cyclohexylmethyl | 30 | 1 | cyclohexylmethyl |
| 15 | 0 | benzyl | 31 | 1 | benzyl |
| 16 | 0 | 4-chlorobenzyl | 32 | 1 | 4-chlorobenzyl |

Salts

The compounds of the present invention of formula (I) may be converted into corresponding salts by conventional methods. Non-toxic and water-soluble salts are preferable. Appropriate salts include salts of alkali metals (potassium, sodium etc.), salts of alkaline-earth metals (calcium, magnesium etc.), ammonium salts and salts of pharmaceutically-acceptable organic amines (tetramethyl ammonium, triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine etc.).

Cyclodextrin Clathrates

The compounds of formula (I) may be converted into cyclodextrin clathrates using α-, β- or γ-cyclodextrin or a mixture thereof, by the methods described in the specification of Japanese Kokoku No. 50-3362, ibid. 52-31404 (i.e. GB Patent Nos. 1351238, 1419221) or Japanese Kokoku No. 61-52146. Converting them into cyclodextrin clathrates serves to increase the stability and solubility in water of the compounds, and therefore it is convenient in the use for pharmaceuticals.

Processes for the Preparation

The compounds of formula (I) may be prepared by the methods described hereafter, by the methods described in the Examples or by known methods.

(1) Among the compounds of the present invention of formula (I), a compound wherein $R^1$ is hydroxy; i.e. a compound of formula (IA)

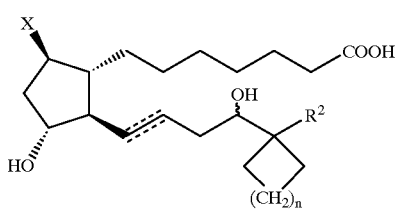
(IA)

(wherein all symbols are as defined hereinbefore.) may be prepared by subjecting to hydrolysis under an alkaline condition a compound among the compounds of formula (I) wherein $R^1$ is C1–6 alkoxy, i.e. a compound of formula (IB)

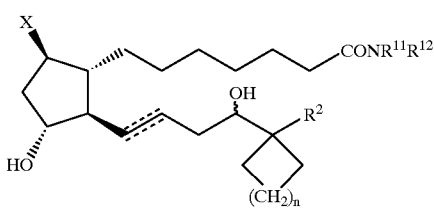
(IB)

(wherein $R^{10}$ is C1–6 alkoxy and the other symbols are as defined hereinbefore.).

Hydrolysis under an alkaline condition is known, for example, it may be carried out in water-miscible organic solvent (methanol, ethanol, tetrahydrofuran, dioxane etc.) using an aqueous solution of an alkali (sodium hydroxide, potassium hydroxide, potassium carbonate etc.) at a temperature of from −10° C. to 90° C.

(2) Among the compounds of the present invention of formula (I), a compound wherein $R^1$ is C1–6 alkoxy, i.e. a compound of formula (IB)

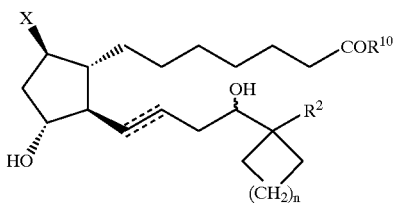
(IB)

(wherein all symbols are as defined hereinbefore.) may be prepared by subjecting to hydrolysis under an acidic condition a compound of formula (II)

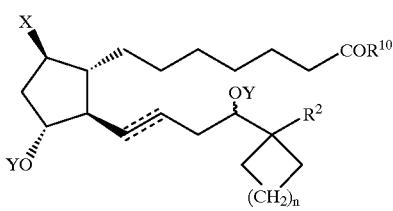
(II)

(wherein Y is a hydroxy-protecting group which may be removed under an acidic condition and the other symbols are as defined hereinbefore.).

Hydrolysis under an acidic condition is known. For example it may be carried out in a water-miscible organic solvent (tetrahydrofuran, methanol, ethanol, dimethoxyethane, acetonitrile, dioxane or a mixture thereof etc.) using inorganic acid (e.g. hydrochloric acid, phosphoric acid, hydrofluoric acid, hydrogen fluoride-pyridine etc.) or organic acid (acetic acid, tosyl acid, trifluoroacetic acid) at a temperature of from 0° C. to 50° C.

(3) Among the compounds of the present invention of formula (I), a compound wherein $R^1$ is $NR^{11}R^{12}$, i.e. a compound of formula (IC)

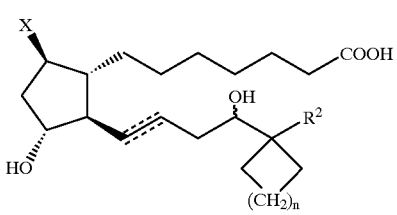
(IC)

(wherein all symbols are as defined hereinbefore.) may be prepared by amidation of a compound of formula (IA)

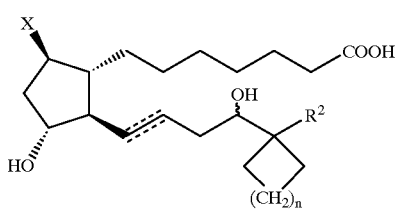
(IA)

(wherein all symbols are as defined hereinbefore.) with a compound of formula (III)

$HNR^{11}R^{12}$ (III)

(wherein all symbols are as defined hereinbefore.).

Amidation is known, for example, it may be carried out in an inert organic solvent (tetrahydrofuran, methylene chloride, benzene, acetone, acetonitrile or a mixture thereof etc.), in the presence or absence of tertiary amine (dimethylaminopyridine, pyridine, triethylamine etc.), using a condensation agent (1,3-dicyclohexylcarbodiimide (DCC), 1-ethyl-3-[3-(dimethylamino)propyl]carbodiimide (EDC) etc.) at a temperature of from 0° C. to 50° C.

(4) Among the compounds of the present invention of formula (I), a compound wherein the bond of 13–14 position is single bond, i.e. a compound of formula (IA-1)

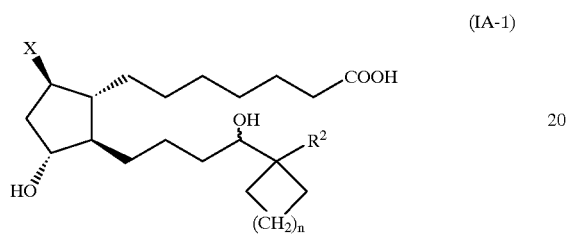

(IA-1)

(wherein all symbols are as defined hereinbefore.) may be prepared by subjecting to reduction a compound of formula (IA-2)

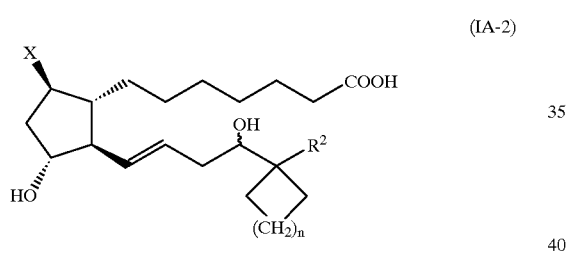

(IA-2)

(wherein all symbols are as defined hereinbefore.).

Reduction is known, for example it may be carried out by hydrogen addition reaction.

Hydrogen addition reaction is known, for example it may be carried out in an inert solvent (e.g. tetrahydrofuran, diethyl ether, methanol, ethanol, dimethylformamide, water, ethyl acetate or acetic acid) or a mixture thereof etc. in the presence of a catalyst for hydrogenation (palladium-carbon, palladium black, palladium hydroxide, platinum dioxide, Raney nickel etc.) in the presence or absence of inorganic acid (hydrochloric acid, sulfuric acid, boric acid etc.) or organic acid (acetic acid, p-toluenesulfonic acid, trifluoroacetic acid etc.) under atmosphere of hydrogen at normal or high pressure, at a temperature of from 0° C. to 200° C. In use of acid, the salts may be used.

A compound of formula (II) may be prepared according to the following reaction schemes (A)–(E).

The symbols described in the reaction schemes (A)–(E) are as defined hereinbefore or represent the followings.

Ms: mesyl,

Ts: tosyl,

Z: a hydroxy-protecting group such as benzyl or a group including silyl

Reaction Scheme (A)

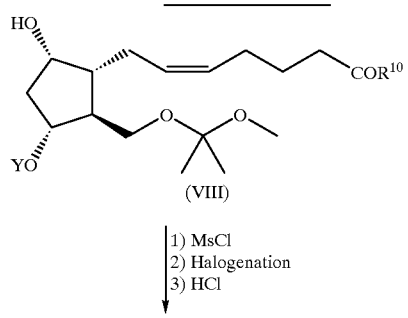

(VIII)

1) MsCl
2) Halogenation
3) HCl

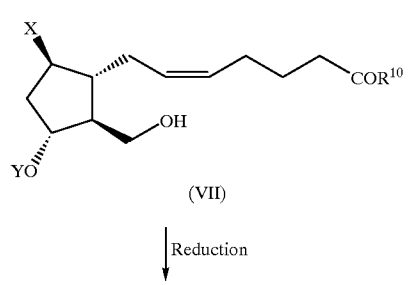

(VII)

Reduction

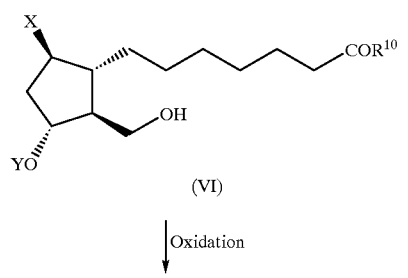

(VI)

Oxidation

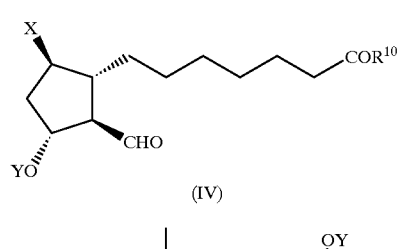

(IV)

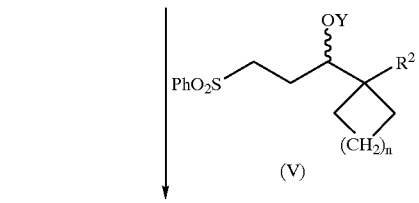

(V)

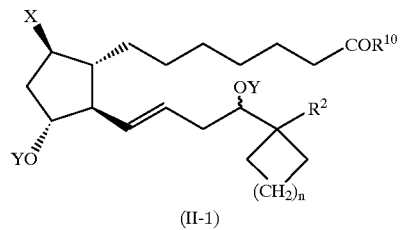

(II-1)

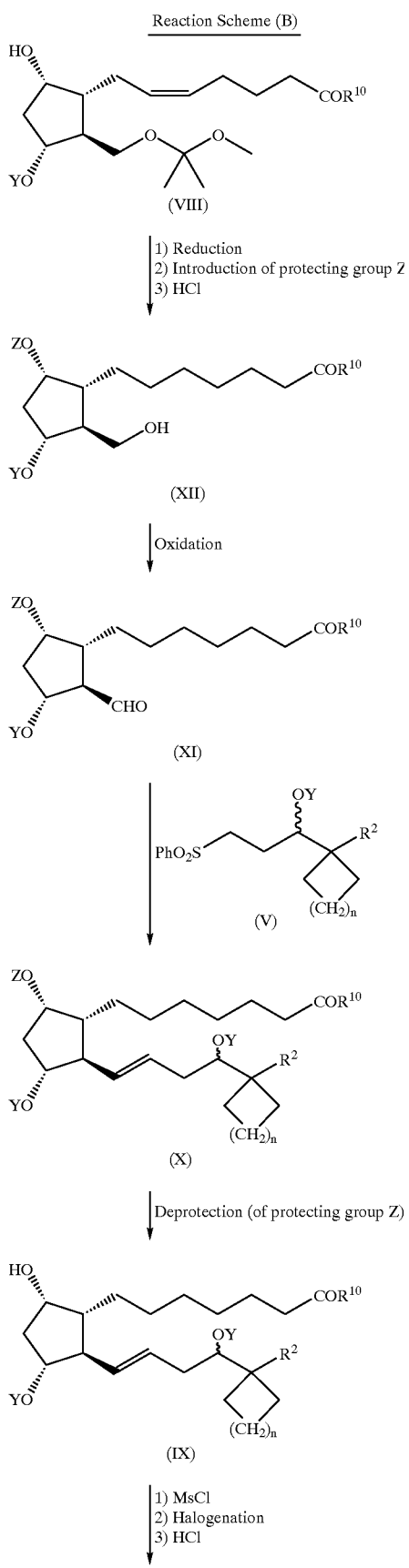
Reaction Scheme (B)
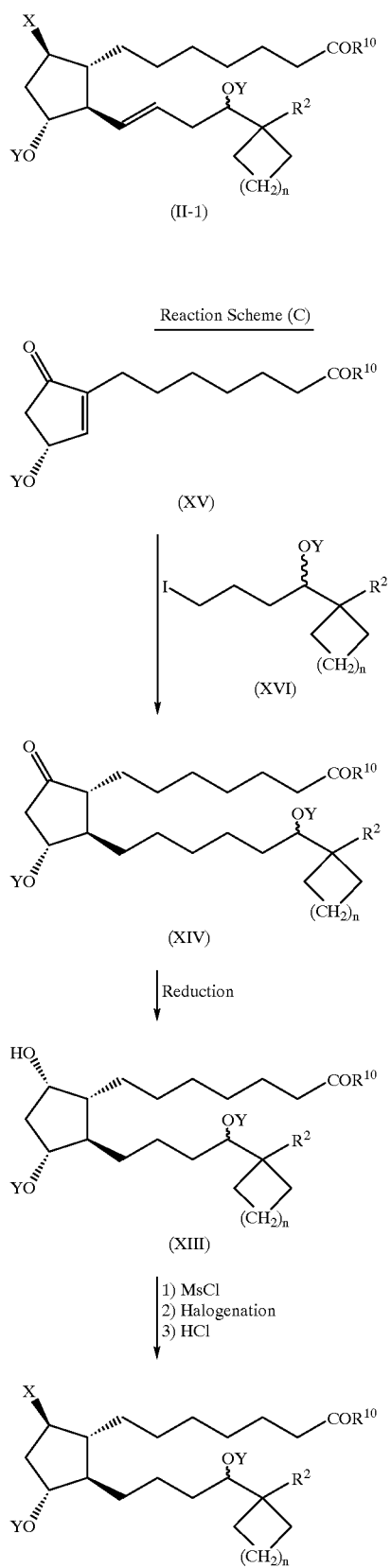
Reaction Scheme (C)

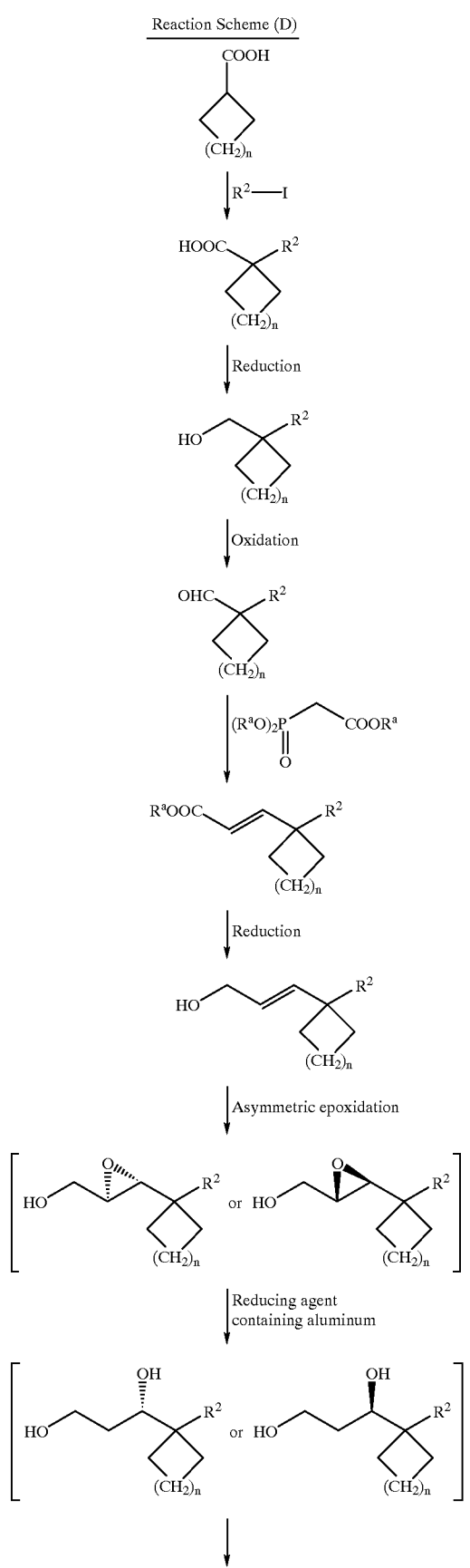
Reaction Scheme (D)
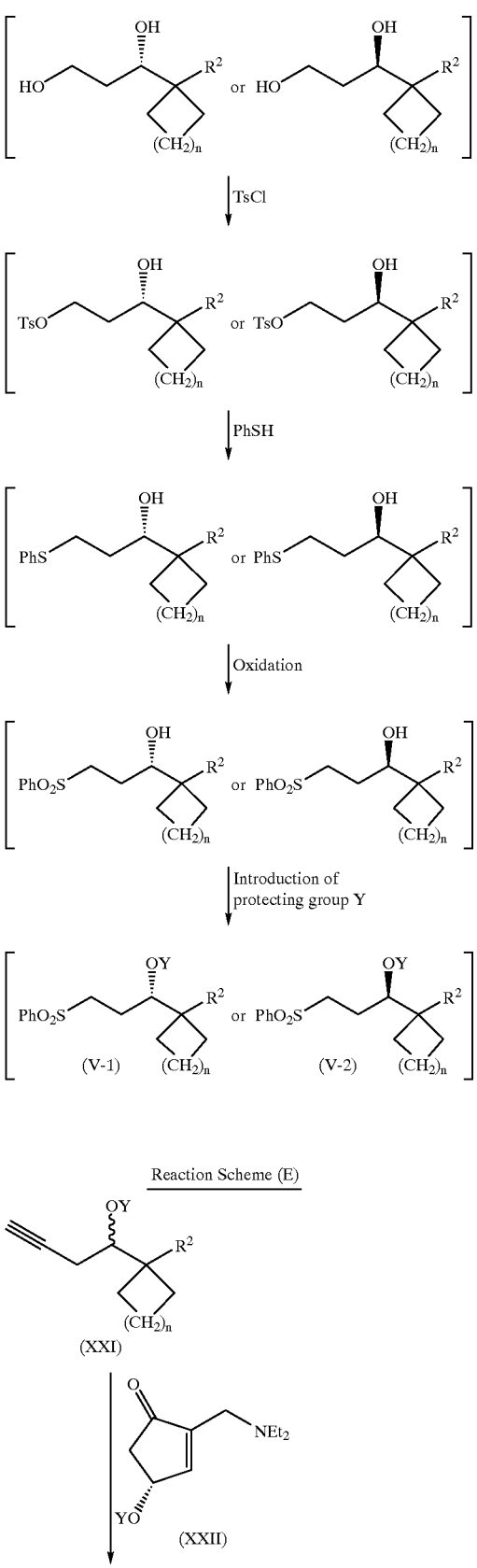
Reaction Scheme (E)

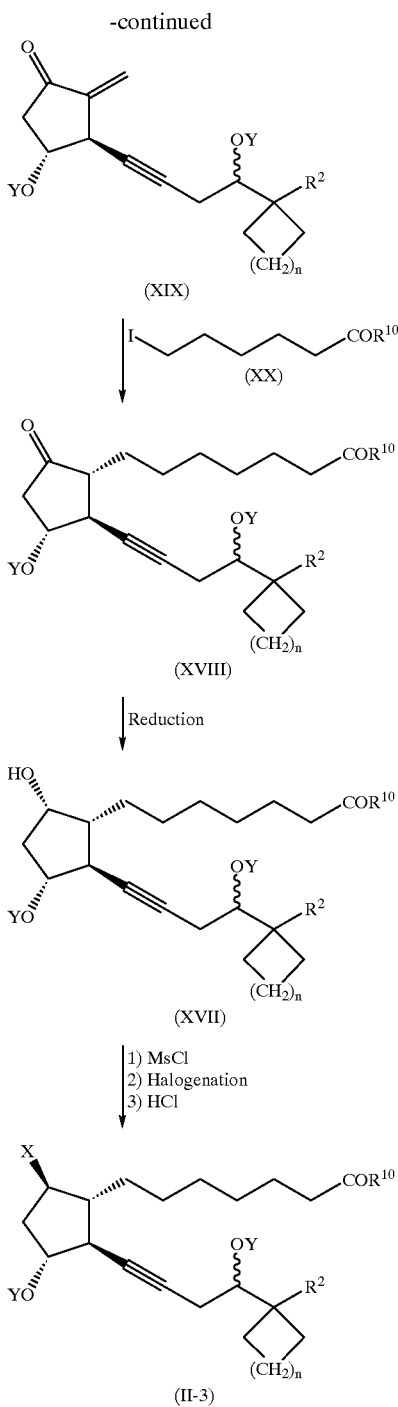

In the reaction schemes hereinbefore described, the compounds used as the starting materials are known per se, or may be easily prepared by known methods.

For example, among the compounds of formula (VIII), a compound wherein $R^{10}$ is methyl and Y is tetrahydropyranyl is described in J. Med. Chem. 23, 525–535 (1980).

The other starting materials and reagents in the present invention are known per se or may be prepared by known methods.

In each reaction of the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activities

The compounds of the present invention of formula (I) bind strongly and act on $EP_2$ receptor which is $PGE_2$ receptor subtype.

For example, in the laboratory the effects of the compounds of the present invention were confirmed by binding assay using expression cell of prostanoids receptor subtype.

(i) Binding assay using expression cell of prostanoids receptor subtype

The preparation of membrane fraction was carried out according to the method of Sugimoto et al. [J. Biol. Chem., 267, 6463–6466 (1992)], using expression CHO cell of the prostanoids receptor subtype (mouse $EP_1$, $EP_2$, $EP_{3\alpha}$, $EP_4$).

The standard assay mixture containing membrane fraction (0.5 mg/ml), and $^3H$-$PGE_2$ in a final volume of 200 $\mu l$ was incubated at room temperature for 1 hour. The reaction was terminated by addition of 3 ml of ice-cooled buffer. The mixture was filtered through a GF/B glass filter under reduced pressure. The radioactivity associated with the filter was measured by liquid scintillation counter.

Kd and Bmax values were determined from Scatchard plots [Ann. N.Y. Acad. Sci., 51, 660 (1949)]. Non-specific binding was calculated as the binding in the presence of an excess (10 $\mu M$) of unlabeled $PGE_2$. In the measurement of $^3H$-$PGE_2$ binding inhibitory activity, 2.5 nM of $^3H$-$PGE_2$ and various concentrations of the compounds of the present invention were added. The following buffer was used in all reactions.

Buffer; 10 mM potassium phosphate (pH 6.0), 1 mM EDTA, 10 mM $MgCl_2$, 0.1 M NaCl.

The dissociation constant Ki ($\mu M$) of each compound was calculated by the following equation.

$$Ki = IC_{50}/(1+([C]/Kd))$$

The results are shown in the Table 7.

TABLE 7

| Example | Dissociation Constant Ki ($\mu M$) | | | |
| No. | $EP_1$ | $EP_2$ | $EP_{3\alpha}$ | $EP_4$ |
| --- | --- | --- | --- | --- |
| 2 | 5.7 | 0.0081 | >10 | 1.7 |
| 2(a) | >10 | 0.066 | >10 | >10 |
| 3(a) | 3.5 | 0.017 | >10 | >10 |

Toxicity

The toxicity of the compounds of the present invention is very low and therefore, it is confirmed that these compounds are safe for pharmaceutical use.

Application to Pharmaceuticals

The compounds of the present invention of formula (I) bind and act on $PGE_2$ receptor and therefore they are useful. Particularly, they strongly bind on $EP_2$ subtype, therefore, they are useful for the prevention and/or treatment of immunological diseases (autoimmune diseases, posttransplantation graft rejection etc.), asthma, abnormal bone formation, neuronal cell death, liver damage, abortion, premature birth or retina neuropathy of glaucoma etc.

Among the compounds of the present invention of formula (I), compounds which bind weakly on other receptor subtypes than $EP_2$ and other receptors of arachidonic acid metabolites (thromboxane receptor, $PGI_2$ receptor etc.) do not express other effects and therefore, it is probable that those compounds will be medical agents which have less side-effects.

For the purpose hereinbefore described, the compounds of the present invention of formula (I), non-toxic salts thereof or cyclodextrin clathrates thereof may normally be administered systemically or locally, by oral or parenteral administration. Converting into prodrugs gives such advantages as less stimulation, better absorbability, better stability etc.

The doses to be administered are determined depending upon age, body weight, symptom, the desired therapeutic effect, the route of administration and the duration of the treatment etc. In the human adult, the doses per person per dose are generally between 1 μg and 100 mg, by oral administration, from once up to several times per day, and between 0.1 μg and 10 mg, by parenteral administration (preferably intravenously) from once up to several times per day, or by continuous administration for between 1 and 24 hours per day into vein.

As mentioned hereinbefore, the doses to be administered depend upon various conditions. Therefore, there are cases in which doses lower than or greater than the ranges specified hereinbefore may be used.

The compounds of the present invention may be administered in the form, for example, of solid compositions, liquid compositions or other compositions for oral administration, or injections, liniments or suppositories etc. for parenteral administration.

Solid compositions for oral administration include compressed tablets, pills, capsules, dispersible powders, granules etc.

Capsules include hard capsules and soft capsules.

In these solid compositions, one or more of the active compound(s) are admixed with at least one inert diluent e.g. lactose, mannitol, mannit, glucose, hydroxypropyl cellulose, microcrystalline cellulose, starch, polyvinylpyrrolidone, magnesium metasilicate aluminate. The compositions may also comprise, as is normal practice, additives except inert diluents: e.g. lubricating agents such as magnesium stearate, disintegrating agents such as cellulose calcium glycolate and agents to assist dissolution such as glutamic acid, aspartic acid. The tablets or pills may, if desired, be coated with film of gastric or enteric material such as sugar, gelatin, hydroxypropyl cellulose or hydroxypropyl cellulose phthalate etc., or be coated with two or more films. Coating may include containment within capsules of absorbable materials such as gelatin.

Liquid compositions for oral administration include pharmaceutically acceptable emulsions, solutions, syrups and elixirs etc. In such liquid compositions, one or more of the active compound(s) may be contained in inert diluent(s) commonly used in the art (e.g. purified water, ethanol). Besides inert diluents, such compositions may also comprise assisting agents (e.g. wetting agents, suspending agents), sweetening agents, flavouring agents, perfuming agents, preserving agents.

Other compositions for oral administration include spray compositions which comprise one or more of the active compound(s) and which may be prepared by known methods per se. Besides inert diluents, spray compositions may comprise stabilizing agents such as sodium hydrogensulfite, stabilizing agents to give isotonicity, isotonic buffer such as sodium chloride, sodium citrate, citric acid. For the preparation of spray compositions, for example, the methods described in the U.S. Pat. Nos. 2,868,691 and ibid. 3,095, 355 may be used.

Injections for parenteral administration include sterile aqueous or non-aqueous solutions, suspensions and emulsions. Aqueous solutions and suspensions include distilled water for injection and physiological salt solution. Non-aqueous solutions or suspensions include e.g. propylene glycol, polyethylene glycol, vegetable oil such as olive oil, alcohol such as ethanol, POLYSORBATE80 (registered trademark) etc. Such compositions may comprise assisting agents: e.g. preserving agents, wetting agents, emulsifying agents, dispersing agents, stabilizing agents, assisting agents such as agents to assist dissolution (for example, glutamic acid, aspartic acid). They may be sterilized for example, by filtration through a bacteria-retaining filter, by incorporation of sterilizing agents or by irradiation.

They may also be manufactured in the form of sterile solid compositions and which may be sterilized or dissolved in sterile distilled water for injection or other sterile solvents before use.

Other compositions for parenteral administration include liquids for externaluse, liniments, ointment, suppositories for rectal administration and pessaries for vaginal administration etc. which comprise one or more of the active compound(s) and may be prepared by conventional methods.

REFERENCE EXAMPLES AND EXAMPLES

The following reference examples and examples are intended to illustrate, but do not limit, the present invention. The solvents in parentheses show the developing or eluting solvents and the ratios of the solvents used are by volume in chromatographic separations. NMR in parentheses show the solvents used in measurement. In the reference examples and examples, Me is methyl, Et is ethyl, Ph is phenyl, Ts is tosyl and THP is tetrahydropyranyl.

Reference Example 1

7-[(1α,2β,3α,5β)-2-Hydroxymethyl-3-tetrahydropyranyloxy-5-chlorocyclopentyl]-5Z-heptenoic acid methyl ester

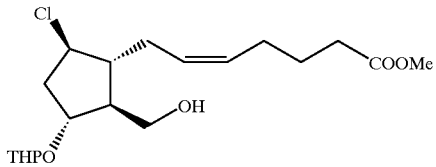

To a solution of 7-[(1α,2β,3α,5α)-2-(1-methyl-1-methoxyethoxymethyl)-3-tetrahydropyranyloxy-5-hydroxycyclopentyl]-5Z-heptenoic acid methyl ester (50.0 g) and triethylamine (48.8 ml) in methylene chloride (250 ml) was added dropwise a solution of mesyl chloride (13.6 ml) in methylene chloride (50 ml) at 0° C. and the mixture was stirred at the temperature for one hour. To the reaction mixture water (200 ml) was added and the mixture was extracted with ethyl acetate twice. The organic layer was washed by water and then a saturated aqueous solution of sodium chloride, dried over anhydrous magnesium sulfate and concentrated to give 7-[(1α,2β,3α,5α)-2-(1-methyl-1-methoxyethoxymethyl)-3-tetrahydropyranyloxy-5-methanesulfonylcyclopentyl]-5Z-heptenoic acid methyl ester.

To a solution of this compound in toluene (600 ml) were added tetrabutylammonium chloride (48.6 g) and potassium carbonate (48.3 g) and the mixture was stirred at 60° C. for 4 hours. The reaction solution was cooled to 20° C. and thereto water (300 ml) was added and the mixture was extracted with ethyl acetate. The organic layer was washed by water and a saturated aqueous solution of sodium chloride, dried over anhydrous magnesium sulfate and concentrated to give 7-[(1α,2β,3α,5β)-2-(1-methyl-1-methoxyethoxymethyl)-3-tetrahydropyranyloxy-5-chlorocyclopentyl]-5Z-heptenoic acid methyl ester (52.0 g).

To a solution of this compound in tetrahydrofuran (THF; 250 ml) was added 0.2 N hydrochloric acid (100 ml) dropwise over a period of one hour at −5° C. and the mixture was stirred at the temperature for 3 hours. To the reaction mixture 1N hydrochloric acid (10 ml) was added dropwise and the mixture was stirred for one hour. To this reaction solution was added a saturated aqueous solution of sodium bicarbonate and was extracted with ethyl acetate. The organic layer was washed by water and a saturated aqueous solution of sodium chloride, dried over anhydrous magnesium sulfate and concentrated. The residue was purified by column chromatography on silica gel (hexane:ethyl acetate= 3:1) to give the title compound (16.5 g) having the following physical data.

TLC: Rf 0.41 (n-hexane:ethyl acetate=1:1);

NMR (CDCl$_3$): δ5.45–5.30 (m, 2H), 4.64–4.48 (m, 1H), 4.30–3.68 (m, 4H), 3.60 (s, 3H), 3.56–3.40 (m, 2H), 2.4–1.4 (m).

Reference Example 2

7-[(1α,2β,3α,5β)-2-Hydroxymethyl-3-tetrahydropyranyloxy-5-chlorocyclopentyl]-heptanoic acid methyl ester

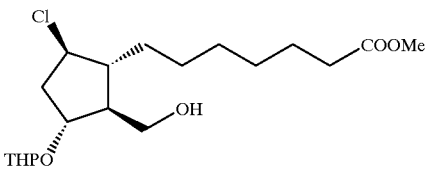

Under atmosphere of argon, a solution of the compound prepared in reference example 1 (500 mg) and 5% palladium-carbon (50 mg) in ethanol (10 ml) was stirred at room temperature for 3 hours. The reaction mixture was filtered through celite (a brand name). The filtrate was concentrated to give the title compound having the following physical data.

TLC: Rf 0.40 (n-hexane:ethyl acetate=1:1);

NMR (CDCl$_3$): δ4.78–4.54 (m, 1H), 4.3–4.3 (m, 6H), 3.67 (s, 3H), 2.31 (t, J=7.5 Hz, 2H), 2.3–2.1 (m, 2H), 2.0–1.2 (m).

Reference Example 3

7-[(1α,2β,3α,5β)-2-Formyl-3-tetrahydropyranyloxy-5-chlorocyclopentyl]heptanoic acid methyl ester

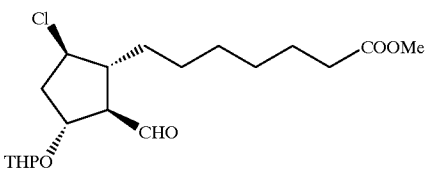

To a solution of the compound prepared in reference example 2 (500 mg) in dimethylsulfoxide/methylene chloride (each 10 ml) was added triethylamine (5 ml). To the mixture in a water bath was added sulfur trioxide-pyridine complex (630 mg) and the mixture was stirred at room temperature for one hour. To the reaction solution was added water and the mixture was extracted with hexane/ethyl acetate (1:1). The organic layer was washed by water and a saturated aqueous solution of sodium chloride, dried over anhydrous magnesium sulfate and concentrated. The residue was purified by column chromatography on silica gel (n-hexane:ethyl acetate=4:1) to give the title compound (452 mg) having the following physical data.

TLC: Rf 0.34 (n-hexane:ethyl acetate=2:1);

NMR (CDCl$_3$): δ9.77 and 9.74 (2d, J=2.0 Hz, 1H), 4.7–4.5 (m, 2H), 4.2–4.0 (m, 1H), 3.9–3.7 (m, 1H), 3.67 (s, 3H), 3.6–3.4 (m, 1H), 2.8–2.0 (m, 6H), 2.0–1.2 (m, 16H).

Reference Example 4

2,2-Propano-1-butanol

To a solution of lithium diisopropylamide (800 ml; 2.0 M THF solution) in THF (800 ml) was added dropwise over a period of 50 minutes under cooling with ice, a solution of cyclobutanecarboxylic acid (80 g) in THF (100 ml) and the mixture was stirred at room temperature for two hours. To the mixture ethyl iodide (64.0 ml) was added dropwise and the mixture was stirred at room temperature overnight. To the reaction solution was added 2N hydrochloric acid and the mixture was extracted with ethyl acetate. The organic layer was washed by water and a saturated aqueous solution of sodium chloride, dried over anhydrous magnesium sulfate and concentrated to give 1-ethylcyclobutanecarboxylic acid (142 g).

To a suspension of lithium aluminum hydride (45.4 g) in THF (800 ml) was added a solution of 1-ethylcyclobutanecarboxylic acid in THF (200 ml) and the mixture was refluxed for 30 minutes. The reaction solution was cooled with ice and thereto was added ether, followed by adding a saturated aqueous solution of sodium sulfate (200 ml) slowly. The mixture was stirred at room temperature until it became white suspension, when thereto was added sodium sulfate and the mixture was filtered and the filtrate was concentrated to give the title compound (122.1 g) having the following physical data.

TLC: Rf 0.45 (n-hexane:ethyl acetate=4:1);

NMR (CDCl$_3$): δ3.54 (2H, m), 1.95–1.40 (9H, m), 0.83 (3H, t, J=7.4 Hz).

Reference Example 5

4,4-Propano-2-hexenoic acid ethyl ester

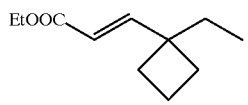

To a solution of oxalyl chloride (70 ml) in methylene chloride (1300 ml) was added dropwise a solution of dimethylsulfoxide (113 ml) in methylene chloride (100 ml) and the mixture was stirred at the temperature for 30 minutes. To this solution was added dropwise a solution of the compound prepared in reference example 4 (61 g) in methylene chloride (100 ml) and the temperature was raised to −40° C. over a period of 30 minutes. To the reaction mixture was added triethylamine (450 ml) dropwise and the temperature was raised to 0° C. over a period of one hour. To the reaction mixture were added water and 2N hydrochloric acid and the mixture was extracted with methylene chloride. The organic layer was washed by water and a saturated aqueous solution of sodium chloride, dried over anhydrous magnesium sulfate and concentrated to give 2-ethylcyclobutanecarboaldehyde.

To a suspension of sodium hydride (41.6 g; 60% in oil) in THF (800 ml) was added dropwise diethylphosphonoethyl acetate (240 ml) under cooling with ice and the mixture was stirred at room temperature for 30 minutes. To the reaction solution was added dropwise 2-ethylcyclobutanecarboaldehyde in THF (200 ml) and the mixture was stirred at room temperature for 30 minutes. Thereto was added a saturated aqueous solution of ammonium chloride and the mixture was extracted with hexane. The organic layer was washed by water and a saturated aqueous solution of sodium chloride, dried over anhydrous magnesium sulfate and concentrated. The residue was purified by column chromatography on silica gel (n-hexane:ethyl acetate=1:0→30:1) to give the title compound (mixture; 95.8 g) having the following physical data.

TLC: Rf 0.44 (n-hexane:ethyl acetate=20:1); NMR (CDCl$_3$): δ6.98 (1H, d, J=15.8 Hz), 5.77 (1H, d, J=15.8 Hz), 4.20 (2H, q, J=7.2 Hz), 2.10–1.80 (6H, m), 1.63 (2H, q, J=7.4 Hz), 1.31 (3H, t, J=7.2 Hz), 0.77 (3H, t, J=7.4 Hz).

Reference Example 6

4,4-Propano-2-hexen-1-ol

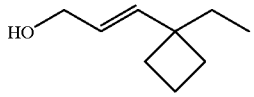

To a solution of the compound prepared in reference example 5 (95.8 g) in THF (800 ml) was added dropwise diisobutylaluminum hydride (800 ml) (1.5M, toluene solution) at −60° C. and the temperature was raised to −10° C. over a period of 30 minutes. To the mixture was added ether, then thereto was added slowly a saturated aqueous solution of sodium sulfate until it became white suspension. Thereto was added sodium sulfate, the mixture was filtered and the filtrate was concentrated. The residue was purified by column chromatography on silica gel (n-hexane:ethyl acetate=10:1) to give the title compound (53.1 g) having the following physical data.

TLC: Rf 0.36 (n-hexane:ethyl acetate=5:1);

NMR (CDCl$_3$): δ5.71 (1H, d, J=15.6 Hz), 5.58 (1H, dt, J=15.6, 5.0 Hz), 4.18 (2H, m), 2.00–1.70 (6H, m), 1.54 (2H, q, J=7.5 Hz), 1.30 (1H, br), 0.75 (3H, t, J=7.5 Hz).

Reference Example 7

(2R,3R)-2,3-Epoxy-4,4-propano-1-hexanol

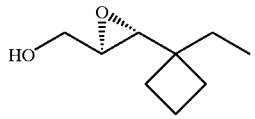

To a suspension of molecular sieves 3 angstrom (36 g; which was dried at 180° C. for 24 hours under reduced pressure) in methylene chloride (400 ml) was added titanium (IV) isopropoxide (21.9 g). To the mixture was added a solution of D-(−)-diisopropyl D-(−)-tartarate (20.8 g) in methylene chloride (100 ml) dropwise at −30° C. and the mixture was stirred at −20° C. for 30 minutes. To this solution was added a compound prepared in reference example 6 (52.0 g) in methylene chloride (150 ml) dropwise and the mixture was stirred at the temperature for 30 minutes. To the reaction mixture was added dropwise t-butylhydroperoxide (111 ml; 5–6 M solution in decane, 555 mmol, calculated as 5M) and at the temperature the mixture was stirred for one hour. To the reaction mixture was added dimethylsulfide (65 ml) dropwise and the mixture was stirred at a temperature of from −20° C. to 0° C. for one hour, followed by adding 10% aqueous solution of (−)-tartaric acid (600 ml) and the mixture was stirred at room temperature for 30 minutes. The reaction solution was filtered through celite and the filtrate was extracted with ethyl acetate. The aqueous layer was re-extracted with a mixture of hexane/ethyl acetate (1:2) (750 ml). The combined organic layers were washed by water and a saturated aqueous solution of sodium chloride, dried over anhydrous magnesium sulfate and concentrated. The residue was dissolved in ether, cooled down to 0° C., added 1N aqueous solution of sodium hydroxide (150 ml) and the mixture was stirred for 30 minutes. The mixture was extracted with ether, washed by a saturated aqueous solution of sodium chloride, dried over anhydrous magnesium sulfate and concentrated to give the title compound (92.6 g) having the following physical data.

TLC: Rf 0.29 (n-hexane:ethyl acetate=4:1).

Reference Example 8

(3S)-4,4-Propanohexan-1,3-diol

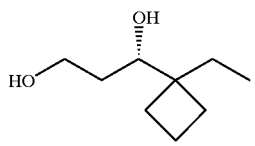

To a solution of sodium bis-(2-methoxyethoxy)aluminum hydride (175 g) in THF (500 ml) was added the compound prepared in reference example 7 in THF (150 ml) at 0° C. and the mixture was stirred at room temperature for 5 hours. To the reaction solution were added methanol and 2N aqueous solution of sodium hydroxide (1.1 l) and the mixture was extracted with toluene (600 ml). The aqueous layer was re-extracted with ethyl acetate and the organic layer was washed by a saturated aqueous solution of sodium chloride, dried over anhydrous magnesium sulfate and concentrated. The residue was purified by column chromatography on silica gel (n-hexane:ethyl acetate=1:1→1:2) to give the title compound (50.8 g) having the following physical data.

TLC: Rf 0.16 (n-hexane:ethyl acetate=1:1);

NMR (CDCl$_3$): δ4.0–3.8 (m, 3H), 2.6–2.2 (m, 2H), 2.0–1.2 (m, 10H), 0.93 (t, J=7.5 Hz, 3H).

Reference Example 9

(3S)-4,4-Propano-1-tosyloxy-3-hexanol

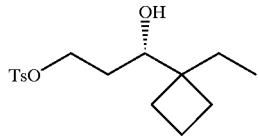

To a solution of the compound prepared in reference example 8 (20.4 g) in pyridine (100 ml) was added tosyl chloride (29.5 g) at 0° C. and the mixture was stirred at the temperature for 15 minutes and at room temperature for one hour. To the reaction mixture was added a small amount of water at 0° C. and the mixture was stirred for 10 minutes, followed by adding water and the mixture was extracted with ethyl acetate. The aqueous layer was re-extracted with ethyl acetate. The combined organic layers were washed by water and a saturated aqueous solution of sodium chloride, dried over anhydrous magnesium sulfate and concentrated to give the title compound (47.1 g) having the following physical data.

TLC: Rf 0.58 (n-hexane:ethyl acetate=2:1);

NMR (CDCl$_3$): δ7.81 (2H, d, J=8.2 Hz), 7.36 (2H, d, J=8.2 Hz), 4.36–4.12 (2H, m), 3.70–3.58 (1H, m), 2.45 (3H, s), 2.00–1.25 (11H, m), 0.88 (3H, t, J=7.3 Hz).

Reference Example 10

(3S)-1-Phenylthio-4,4-propano-3-hexanol

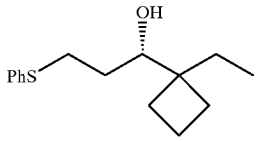

To a solution of thiophenol (13.2 ml) and potassium carbonate (27.0 g) in THF (200 ml) was added dropwise a solution of the compound prepared in reference example 9 (47.1 g) in THF (50 ml) and the mixture was stirred at room temperature for one hour and at 60° C. for one hour. To the reaction solution was added water and the mixture was extracted with ethyl acetate. The organic layer was washed by water and a saturated aqueous solution of sodium chloride, dried over anhydrous magnesium sulfate and concentrated to give the title compound (32.1 g) having the following physical data.

TLC: Rf 0.58 (n-hexane:ethyl acetate=4:1);

NMR (CDCl$_3$): δ7.40–7.10 (5H, m), 3.80–3.65 (1H, m), 3.28–2.94 (2H, m), 2.00–1.20 (11H, m), 0.88 (3H, t, J=7.5 Hz).

Reference Example 11

(3S)-3-Hydroxy-4,4-propanohexylphenylsulfone

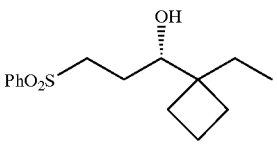

To a solution of the compound prepared in reference example 10 (32.1 g) in methanol (500 ml) was added dropwise a solution of oxon (115.4 g) in water (500 ml) under cooling with ice. The mixture was stirred at room temperature for one hour, followed by adding an aqueous solution of sodium thiosulfate, and the mixture was stirred at room temperature for 10 minutes. The suspension was filtered. To the filtrate was added water and the mixture was extracted with ethyl acetate. The organic layer was washed by water and a saturated aqueous solution of sodium chloride, dried over anhydrous magnesium sulfate and concentrated to give the title compound (30.0 g) having the following physical data.

TLC: Rf 0.32 (n-hexane:ethyl acetate=2:1);

NMR (CDCl$_3$): δ8.00–7.90 (2H, m), 7.70–7.50 (3H, m), 3.66–3.55 (1H, m), 3.50–3.10 (2H, m), 2.00–1.30 (11H, m), 0.88 (3H, t, J=7.5 Hz).

Reference Example 12

(3S)-3-Tetrahydropyranyloxy-4,4-propanohexylphenylsulfone

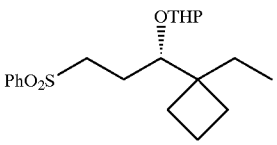

To a solution of the compound prepared in reference example 11 (30 g) and dihydropyran (9.6 ml) in methylene chloride (250 ml) was added pyridinium p-toluenesulfonate (1.76 g) and the mixture was stirred at room temperature for 3 hours. To the reaction solution was added a saturated aqueous solution of sodium bicarbonate and the mixture was extracted with a mixture of hexane/ethyl acetate (1:1). The organic layer was washed by water and a saturated aqueous solution of sodium chloride. The residue was purified by column chromatography on silica gel (hexane:ethyl acetate=8:1) to give the title compound (22.5 g) having the following physical data.

TLC: Rf 0.42 and 0.37 (n-hexane:ethyl acetate=4:1);

NMR (CDCl$_3$): δ8.00–7.90 (2H, m), 7.70–7.50 (3H, m), 3.66–3.55 (1H, m), 3.50–3.10(2H, m), 2.00–1.30 (11H, m), 0.88 (3H, t, J=7.5 Hz).

Reference Example 13

(9β,11α,16α)-9-Chloro-11,16-bis(tetrahydropyranyloxy)-17,17-propano-20-norprosta-13E-enoic acid methyl ester

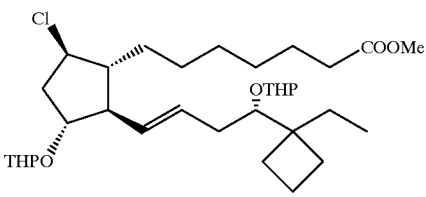

To a solution of the compound prepared in reference example 12 (530 mg) in THF (4 ml) was added dropwise n-butyl lithium (940 μl; 1.53 M, n-hexane solution) and the mixture was stirred at −78° C. for one hour. This solution was added to a solution of the compound prepared in reference example 3 (450 mg) in THF (6 ml) at −78° C. and the mixture was stirred at the temperature for one hour. To the reaction solution was added acetic anhydride (340 μl) and the mixture was stirred for one hour and the temperature was raised to 0° C. To the reaction solution was added a saturated aqueous solution of ammonium chloride and the mixture was extracted with ethyl acetate. The organic layer was washed by water and a saturated aqueous solution of sodium chloride, dried over anhydrous magnesium sulfate and concentrated to give acetoxysulfonated compound. To a solution thereof in anhydrous methanol (10 ml) was added magnesium powder (30 mg) and trimethylsilyl chloride (30 μl) and the mixture was stirred at room temperature for two hours. To the reaction solution was added a saturated aqueous solution of ammonium chloride and the mixture was extracted with ethyl acetate. The organic layer was washed by water and a saturated aqueous solution of sodium chloride, dried over anhydrous magnesium sulfate and concentrated. The residue was purified by column chromatography on silica gel (n-hexane:ethyl acetate=8:1) to give the title compound (260 mg) having the following physical data.

TLC: Rf 0.56 (n-hexane:ethyl acetate 2:1).

Example 1

(9β,11α,16α)-9-Chloro-11,16-dihydroxy-17,17-propano-20-norprosta-13E-enoic acid methyl ester

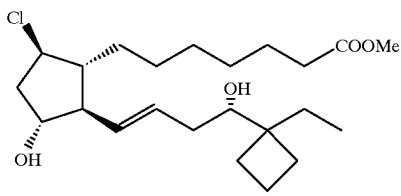

The compound prepared in reference example 13 (255 mg) was dissolved in a mixture of methanol (1 ml) and 4N hydrochloric acid/1,4-dioxane (100 μl), and the mixture was stirred at room temperature for one hour. To the reaction solution was added a saturated aqueous solution of sodium bicarbonate and the mixture was extracted with ethyl acetate. The organic layer was washed by water and a saturated aqueous solution of sodium chloride, dried over anhydrous magnesium sulfate and concentrated. The residue was purified by column chromatography on silica gel (n-hexane:ethyl acetate=2:1) to give the title compound (103 mg) having the following physical data.

TLC: Rf 0.27 (n-hexane:ethyl acetate=1:1);

NMR (CDCl$_3$): δ5.57 (ddd, J=15, 8, 6 Hz, 1H), 5.41 (dd, J=15, 8 Hz, 1H), 4.10(q, J=8 Hz, 1H), 4.03–3.97 (m, 1H), 3.67 (s, 3H), 3.53 (dd, J=10, 2 Hz, 1H) , 2.30 (t, J=7.5 Hz, 2H) ,2.3–1.2 (m, 24H) , 0.92 (t, J=7.5 Hz, 3H).

Example 1(a)

(9β,11α,16α)-9-Fluoro-11,16-dihydroxy-17,17-propano-20-norprosta-13E-enoic acid methyl ester

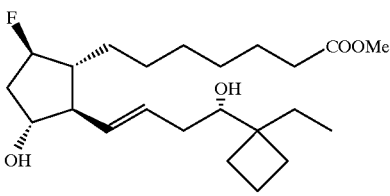

By the same procedure as described in reference example 1 using tetrabutylammonium fluoride in place of tetrabutylammonium chloride, followed by the same procedure for preparing the compound of example 1, the title compound having the following physical data was obtained.

TLC: Rf 0.50 (n-hexane:ethyl acetate=1:1);

NMR (CDCl$_3$): δ5.58 (ddd, J=15.4, 8.0, 5.4 Hz, 1H), 5.41 (dd, J=15.4, 8.4 Hz, 1H), 4.87 and 4.60 (m(J(F–H)=54 Hz), 1H), 4.12–3.98 (m, 1H), 3.67 (s, 3H), 3.54 (dd, J=10.0, 2.4 Hz, 1H), 2.40–1.20 (m, 26H), 2.30 (t, J=7.5 Hz, 2H), 0.92 (t, J=7.5 Hz, 3H).

Example 2

(9β,11α,16α)-9-Chloro-11,16-dihydroxy-17,17-propano-20-norprosta-13E-enoic acid

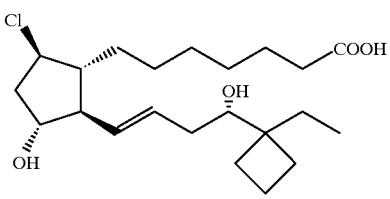

To a solution of the compound prepared in example 1 (80 mg) in methanol (1 ml) was added 2N aqueous solution of sodium hydroxide (0.5 ml) and the mixture was stirred at room temperature for 4 hours. The mixture was acidified by adding 2N hydrochloric acid and the mixture was extracted with ethyl acetate. The organic layer was washed by water and a saturated aqueous solution of sodium chloride, dried over anhydrous magnesium sulfate and concentrated. The residue was purified by column chromatography on silica gel (n-hexane:ethyl acetate=1:1→0:1) to give the title compound (61 mg) having the following physical data.

TLC: Rf 0.47 (chloroform:methanol=9:1);

NMR (CDCl$_3$): δ5.63–5.53 (m, 1H), 5.42 (dd, J=15, 8 Hz, 1H), 4.16–4.08 (m, 1H), 4.04–3.98 (m, 1H), 3.56 (dd, J=10, 2 Hz, 1H), 2.34 (t, J=7.5 Hz, 2H), 2.3–1.2 (m, 24H), 0.92 (t, J=7.5 Hz, 3H).

Example 2(a)

(9β,11α,16α)-9-Fluoro-11,16-dihydroxy-17,17-propano-20-norprosta-13E-enoic acid

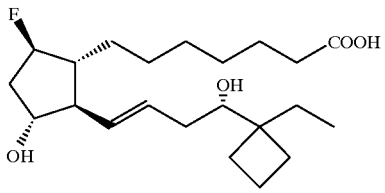

By the same procedure as described in example 2 using the compound prepared in example 1(a) in place of the compound prepared in example 1, the title compound having the following physical data was obtained.

TLC: Rf 0.28 (n-hexane:ethyl acetate:acetic acid= 1:1:0.02);

NMR (CDCl$_3$): δ5.58 (ddd, J=15.4, 7.6, 5.4 Hz, 1H), 5.42 (dd, J=15.4, 7.8 Hz, 1H), 4.87 and 4.60 (m(J(F–H)=54 Hz), 1H), 4.50–3.50 (br, 3H), 4.15–3.98 (m, 1H), 3.56 (dd, J=10.2, 2.4 Hz, 1H), 2.40–1.20 (m, 24H), 2.34 (t, J=7.1 Hz, 2H), 0.92 (t, J=7.3 Hz, 3H).

Example 3

(9β,11α,16α)-9-Fluoro-11,16-dihydroxy-17,17-propano-20-norprostanoic acid methyl ester

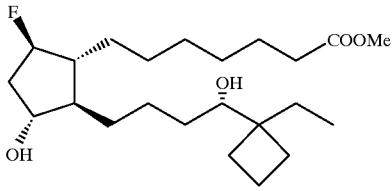

To a solution of the compound prepared in example 1(a) (250 mg) in methanol (2 ml) under atmosphere of argon was added palladium carbon (25 mg) and the mixture was stirred under atmosphere of hydrogen at room temperature for 6 hours. The suspension was filtered and the filtrate was concentrated. The residue was purified by column chromatography on silica gel (n-hexane:ethyl acetate=1:1) to give the title compound (131 mg) having the following physical data.

TLC: Rf 0.43 (n-hexane:ethyl acetate=1:1);

NMR (CDCl$_3$): δ4.77 (ddt, J=54, 5.6, 3.2 Hz, 1H), 4.10 (m, 1H), 3.67 (s, 3H), 3.55 (d, J=9.6 Hz, 1H), 2.31 (t, J=7.3 Hz, 2H), 2.30–1.20 (m, 30H), 0.92 (t, J=7.5 Hz, 3H).

Example 3(a)

(9β,11α,16α)-9-Chloro-11,16-dihydroxy-17,17-propano-20-norprostanoic acid

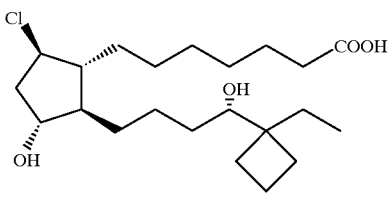

By the same procedure as described in example 3 using the compound prepared in example 2 in place of the compound prepared in example 1(a), the title compound having the following physical data was obtained.

TLC: Rf 0.37 (n-hexane:ethyl acetate:acetic acid= 1:1:0.02);

NMR (CDCl$_3$): δ4.50–2.50 (br, 3H), 4.17–3.98 (m, 2H), 3.57 (d, J=9.0 Hz, 1H), 2.35 (t, J=7.0 Hz, 2H), 2.14 (dd, J=7.0, 5.8 Hz, 2H), 2.00–1.20 (m, 26H), 0.92 (t, J=7.5 Hz, 3H).

Example 4

(9β,11α,16α)-9-Fluoro-11,16-dihydroxy-17,17-propano-20-norprostanoic acid

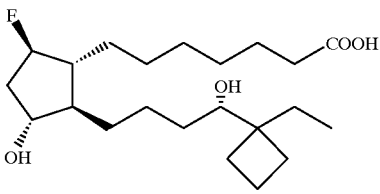

By the same procedure as described in example 2 using the compound prepared in example 3 in place of the compound prepared in example 1, the title compound having the following physical data was obtained.

TLC: Rf 0.30 (n-hexane:ethyl acetate:acetic acid= 1:1:0.02);

NMR (CDCl$_3$): δ4.77 (ddt, J=54, 5.6, 3.0 Hz, 1H), 4.09 (m, 1H), 3.60 (br, 3H), 3.58 (d, J=9.2 Hz, 1H), 2.35 (t, J=7.2 Hz, 2H), 2.30–1.20 (m, 28H), 0.92 (t, J=7.5 Hz, 3H).

Formulation Example

Formulation Example 1

The following compounds were admixed in a conventional method, dried, added microcrystalline cellulose, mixed until homogeneous and punched out to obtain 100 tablets each containing 30 μg of active ingredient.

| | |
|---|---|
| (9 β, 11 α, 16 α)-9-Chloro-11,16-dihydroxy-17,17-propano-20-norprosta-13E-enoic acid (3 mg) in ethanol | 10 mL |
| Magnesium stearate | 100 mL |
| silicon dioxide | 20 mg |
| talc | 10 mg |

| | |
|---|---|
| -continued | |
| Carboxymethylcellulose calcium | 200 mg |
| Microcrystalline cellulose | 5.0 g |

What is claimed is:

1. An ω-cycloalkyl-prostaglandin $E_1$ derivatives of the formula (I)

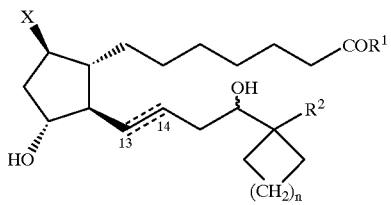

(I)

wherein $R^1$ is hydroxy, C1–6 alkoxy or $NR^{11}R^{12}$ wherein $R^{11}$ and $R^{12}$ are independently hydrogen atom or C1–6 alkyl;

X is chlorine atom or fluorine atom;

$R^2$ is hydrogen atom, C1–8 alkyl, C2–8 alkenyl or C2–8 alkynyl, or C1–8 alkyl, C2–8 alkenyl or C2–8 alkynyl substituted by 1–3 of the following groups (1)~(5):
 (1) halogen atom,
 (2) C1–4 alkoxy,
 (3) C3–7 cycloalkyl,
 (4) phenyl,
 (5) phenyl substituted by 1–3 substituents selected from halogen, C1–4 alkyl, C1–4 alkoxy, nitro and trifluoromethyl;

n is 0–4; and

is single-bond, double-bond or triple-bond; or a non-toxic salt thereof or a cyclodextrin clathrate thereof.

2. A compound according to claim 1 wherein $R^1$ is hydroxy.

3. A compound according to claim 1 wherein $R^1$ is C1–6 alkoxy.

4. A compound according to claim 1 wherein $R^1$ is $NR^{11}R^{12}$ wherein $R^{11}$ and $R^{12}$ are independently hydrogen atom or C1–6 alkyl.

5. A compound according to claim 1 wherein $R^2$ is hydrogen atom.

6. A compound according to claim 1 wherein $R^2$ is C1–8 alkyl.

7. A compound according to claim 1 wherein $R^2$ is C2–8 alkenyl.

8. A compound according to claim 1 wherein $R^2$ is C2–8 alkynyl.

9. A compound according to claim 1 wherein $R^2$ is C1–8 alkyl substituted by 1–3 of the following groups (1)~(5):
 (1) halogen atom,
 (2) C1–4 alkoxy,
 (3) C3–7 cycloalkyl,
 (4) phenyl,
 (5) phenyl substituted by 1–3 substituents selected from halogen, C1–4 alkyl, C1–4 alkoxy, nitro and trifluoromethyl.

10. A compound according to claim 1 wherein $R^2$ is C2–8 alkenyl substituted by 1–3 of the following groups (1)~(5):
 (1) halogen atom,
 (2) C1–4 alkoxy,
 (3) C3–7 cycloalkyl,
 (4) phenyl or
 (5) phenyl substituted by 1–3 substituents selected from of halogen, C1–4 alkyl, C1–4 alkoxy, nitro or trifluoromethyl.

11. A compound according to claim 1 wherein $R^2$ is C2–8 alkynyl substituted by 1–3 of the following group of (1)~(5);
 (1) halogen atom,
 (2) C1–4 alkoxy,
 (3) C3–7 cycloalkyl,
 (4) phenyl or
 (5) phenyl substituted by 1–3 substituents selected from of halogen, C1–4 alkyl, C1–4 alkoxy, nitro or trifluoromethyl.

12. A compound according to claim 1, which is
 (1) (9β,11α,16α)-9-Chloro-11,16-dihydroxy-17,17-propano-20-norprosta-13E-enoic acid methyl ester,
 (2) (9β,11α,16α)-9-Fluoro-11,16-dihydroxy-17,17-propano-20-norprosta-13E-enoic acid methyl ester,
 (3) (9β,11α,16α)-9-Chloro-11,16-dihydroxy-17,17-propano-20-norprosta-13E-enoic acid,
 (4) (9β,11α,16α)-9-Fluoro-11,16-dihydroxy-17,17-propano-20-norprosta-13E-enoic acid,
 (5) (9β,11α,16α)-9-Fluoro-11,16-dihydroxy-17,17-propano-20-norprostanoic acid methyl ester,
 (6) (9β,11α,16α)-9-Chloro-11,16-dihydroxy-17,17-propano-20-norprostanoic acid, or
 (7) (9β,11α,16α)-9-Fluoro-11,16-dihydroxy-17,17-propano-20-norprostanoic acid.

13. A process for the preparation of a compound of formula (IA)

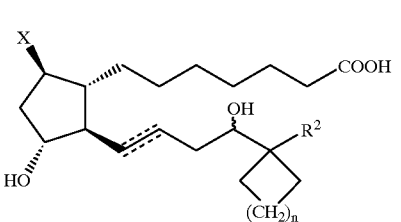

(IA)

wherein all symbols are as defined in claim 1 which comprises hydrolysis under alkaline conditions of a compound of formula (IB)

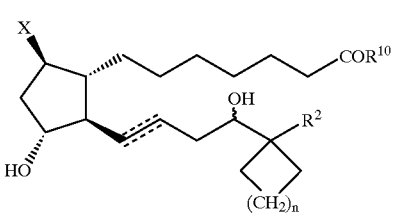

(IB)

wherein $R^{10}$ is C1–6 alkoxy and the other symbols are as hereinbefore defined.

14. A process for the preparation of a compound of formula (IB)

(IB)

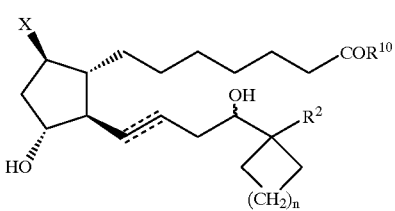

wherein all symbols are as defined in claim 13 which comprises hydrolysis under acidic conditions of a compound of formula (II)

(II)

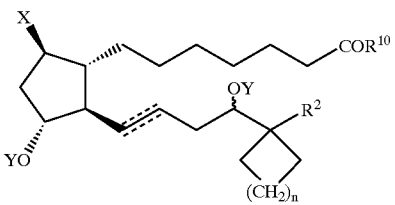

wherein Y is a hydroxy-protecting group which may be removed under acidic conditions and the other symbols are as hereinbefore defined.

15. A process for the preparation of a compound of formula (IC)

(IC)

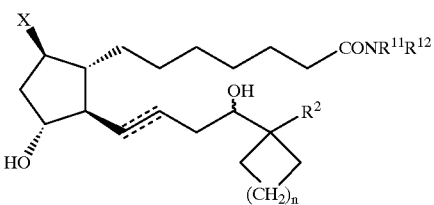

wherein all symbols are as defined in claim 1 which comprises amidation of a compound of formula (IA)

(IA)

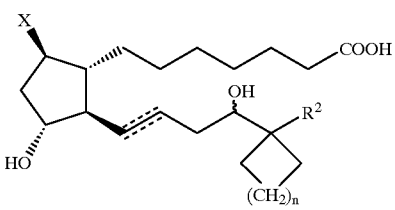

wherein all symbols are as hereinbefore defined with a compound of formula (III)

$$HNR^{11}R^{12}$$ (III)

wherein all symbols are as hereinbefore defined.

16. A process for the preparation of a compound of formula (IA-1)

(IA-1)

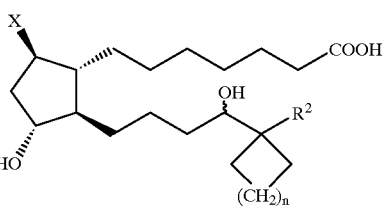

wherein all symbols are as defined in claim 1 which comprises reduction of a compound of formula (IA-2)

(IA-2)

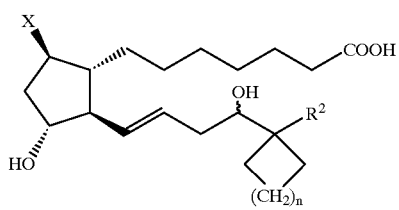

wherein all symbols are as hereinbefore defined.

17. A pharmaceutical composition comprising an ω-cycloalkyl-prostaglandin $E_1$ derivative of formula (I) as defined in claim 1, or a non-toxic salt thereof or cyclodextrin clathrate thereof, as an active ingredient.

18. A method for the prevention and/or the treatment in animals of a disease or condition selected from the group consisting of asthma and retina neuropathy, which method comprises the administration to a patient of an effective amount of an ω-cycloalkyl-prostaglandin E1 derivative of formula (I) as defined in claim 1, a non-toxic salt thereof or a cyclodextrin clathrate thereof.

19. The method according to claim 18, wherein said animal is man.

* * * * *